(12) United States Patent
Helmer (10) Patent No.: US 8,864,722 B2
(45) Date of Patent: Oct. 21, 2014

(54) CARTRIDGE HOLDER AND DRUG DELIVERY DEVICE

(75) Inventor: Michael Helmer, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 199 days.

(21) Appl. No.: 13/290,893

(22) Filed: Nov. 7, 2011

(65) Prior Publication Data

US 2012/0150126 A1 Jun. 14, 2012

(30) Foreign Application Priority Data

Nov. 19, 2010 (EP) ..................................... 10191800

(51) Int. Cl.
| | | |
|---|---|---|
| *A61M 5/00* | (2006.01) | |
| *A61M 37/00* | (2006.01) | |
| *A61M 5/315* | (2006.01) | |
| *A61M 5/24* | (2006.01) | |

(52) U.S. Cl.
CPC ............. *A61M 5/31533* (2013.01); *A61M 5/24* (2013.01); *A61M 5/31525* (2013.01)
USPC ............................ 604/232; 604/131; 604/234

(58) Field of Classification Search
CPC ....... A61M 5/20; A61M 5/204; A61M 5/283; A61M 5/24; A61M 2005/2485; A61M 2005/2492; A61M 2005/2411; A61M 2005/2496; A61M 2005/2488; A61M 2005/2407
See application file for complete search history.

(56) References Cited

U.S. PATENT DOCUMENTS

| 2006/0184117 A1 | 8/2006 | Knight et al. |
| 2011/0046566 A1* | 2/2011 | Elahi et al. ................... 604/214 |

FOREIGN PATENT DOCUMENTS

| EP | 1683537 | 7/2006 |
| WO | 2008/000827 | 1/2008 |
| WO | 2008/059063 | 5/2008 |
| WO | 2008/062025 | 5/2008 |
| WO | 2008/074897 | 6/2008 |

OTHER PUBLICATIONS

European Search Report for EP App. No. 101911800, dated Apr. 5, 2011.

* cited by examiner

*Primary Examiner* — Nathan R Price
(74) *Attorney, Agent, or Firm* — McDonnell Boehnen Hulbert & Berghoff LLP (57) ABSTRACT

The present invention relates to a cartridge holder for a drug delivery device comprising: a distal portion for receiving a cartridge filled with a medicament to be dispensed by the drug delivery device, wherein the distal portion comprises a mount for a piercing assembly, a proximal portion adapted to at least partially receive a drive mechanism having a piston rod to become operably engaged with a piston of the cartridge for expelling a dose of the medicament from the cartridge, wherein the drive mechanism comprises at least first fixing means corresponding with fixing means of the drive mechanism for directly interconnecting cartridge holder and drive mechanism.

8 Claims, 6 Drawing Sheets

CARTRIDGE HOLDER AND DRUG DELIVERY DEVICE

CROSS REFERENCE TO RELATED APPLICATIONS

The present application claims priority to European Patent Application No. 10191800.1 filed Nov. 19, 2010, the entire contents of which are incorporated herein by reference.

FIELD OF THE INVENTION

The present invention relates to a cartridge holder of a drug delivery device that allows a user to select single or multiple doses of an injectable medicament and to dispense the set dosage of the product and to apply said product to a patient, preferably by injection. In particular, the present invention relates to such devices, which are handled by the patients themselves such as pen-type injectors.

BACKGROUND

Drug delivery devices allowing for multiple dosing of a required dosage of a liquid medicinal product and further providing administration of such liquid drug to a patient, are as such well-known in the prior art. Generally, such devices have substantially the same purpose as that of an ordinary syringe.

Drug delivery devices of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

Typically, the medicament to be administered is provided in a cartridge having a moveable piston or bung mechanically interacting with a piston rod of a drive mechanism of the drug delivery device. By applying thrust to the piston in distal direction, a certain and pre-defined amount of the medicinal fluid is expelled from the cartridge.

Drug delivery devices, such as e.g. pen-type injectors, typically comprise a cartridge containing the medicament and a cartridge holder adapted to receive the cartridge and to serve as a mount for a replaceable needle assembly to be coupled with the inner volume of the cartridge in a fluid transferring way. For expelling a predefined dose of the medicament, the drug delivery device further comprises a drive mechanism having a piston rod to become operably engaged with the movable piston of the cartridge for exerting pressure to the piston in a distal direction.

The drive mechanism is typically mounted in a proximal housing section or in a body of the drug delivery device. In a final assembly, the cartridge holder and said body are interconnected. When generating or applying an injection force, a respective counterforce flows across at least two mechanical interfaces, e.g. from the drive mechanism to the body and from the body to the cartridge holder. However, each functional group and interface between functional groups of the drug delivery device inevitably introduce geometric tolerances to the mechanical force transmission system of such devices.

Prior to a first use of the device it most often necessary that the use conducts a setup procedure in order to ensure that the piston rod of the drive mechanism is in direct contact with piston of the cartridge. This setup step is necessary to ensure, that with a first injection procedure a correct and amount of the medicament is precisely dispensed.

Also, different medicaments and dosing instructions may require different device settings or usage of differently labelled drug delivery devices. Hence, there is a need to provide a large variety of drug delivery devices with different outer appearances.

OBJECT OF THE INVENTION

It is therefore an object of the present invention to provide a cartridge holder and a drug delivery device that are simply and easy to assemble and wherein functional components of the drug delivery can be arbitrarily replaced. It is a further object of the present invention to reduce mechanical and geometric tolerances of a drug delivery device and in particular to provide improved interconnectability and inter-operability of movable and functional components of the drug delivery device.

SUMMARY

In one aspect, the present invention relates to a cartridge holder for a drug delivery device, in particular for drug delivery devices such like pen-type injectors. The cartridge holder comprises a distal portion for receiving a cartridge, e.g. an ampoule or carpule filled with a medicament to be dispensed by the drug delivery device. The distal portion of the cartridge holder further comprises a mount for a piercing assembly, such like a needle holder. By mounting the piercing assembly to the distal portion of the cartridge holder a needle element of the piercing assembly may penetrate a pierceable septum of the cartridge, thus providing a fluid communication with the inner volume of the cartridge.

In this context, the distal direction points towards biological tissue the dose of the medicament is administered to. Proximal direction points in the opposite direction, away from the area of application.

The cartridge itself comprises a container, preferably made of glass which is sealed in distal direction by means of a pierceable septum and which is sealed in proximal direction with a piston moveably disposed therein. Upon exertion of pressure to the piston in distal direction, the medicament can be expelled from the cartridge and can be administered to biological tissue by way of an injection needle of the piercing assembly.

The cartridge holder further comprises a proximal portion which is adapted to at least partially receive a drive mechanism of the drug delivery device. The drive mechanism further comprises a piston rod to become operably engaged with the piston of the cartridge for exerting respective distally directed thrust to the piston for moving said piston in distal direction and for expelling a dose of the medicament from the cartridge. Moreover, the cartridge holder comprises at least first fixing means that correspond with fixing means of the drive mechanism for directly interconnecting cartridge holder and drive mechanism.

In this way a direct mutual mechanical engagement of drive mechanism and cartridge can be provided by a single component, preferably by the cartridge holder. The cartridge holder inherently provides a receptacle and fastening means for the cartridge to be arranged therein and further comprises a first fixing means for directly interconnecting cartridge holder and drive mechanism. During dispensing of a dose, the drive mechanism exerts distally directed thrust to the piston and generates an oppositely directed counterforce, which can be directly absorbed by the cartridge holder. Since cartridge holder and cartridge comprise mutually corresponding inner and outer shapes, the cartridge can be secured and retained in the cartridge holder, e.g. by way of a mutual axial abutment.

Since proximal portion and distal portion of the cartridge holder are preferably integrally formed as a single piece, a counterforce initiated by the drive mechanism and acting in proximal direction to the proximal portion of the cartridge holder can be transferred as a retaining force to the cartridge fixed and secured in a distal portion of the cartridge holder.

In this way, potential disadvantages arising from system-inherent geometric tolerances can be reduced. Any system inherent tolerances between a proximal housing portion and the drive mechanism as well as tolerances in an interface of drive mechanism and dose button do no longer have a substantial influence on the dose injecting procedure.

Moreover, by reducing geometric tolerances, even the initializing set-up step could be eliminated.

In a further embodiment, the proximal portion of the cartridge holder comprises a receptacle to receive at least a distal portion of the drive mechanism. Preferably, the drive mechanism is only partially inserted into the proximal portion of the cartridge holder. In an assembly configuration, the proximal end section of the drive mechanism may protrude from the proximal portion of the cartridge holder, thus facilitating further assembly of a dose button and/or a housing component thereto.

According to another preferred embodiment, the cartridge holder comprises second fixing means for directly interconnecting the cartridge holder with a proximal housing component adapted to house at least a proximal portion of the drive mechanism. The proximal housing portion comprises a sleeve-like geometry and is of hollow structure. The proximal housing component is further adapted to be directly interconnected with the cartridge holder but it is neither directly interconnected nor operably engaged with the drive mechanism. The proximal housing component or body of the drug delivery devices only serve as an outer protective sleeve for the drug delivery device and in particular of its drive mechanism.

Preferably, first and second fixing means of the cartridge holder are separated from each other in axial direction. They may further be arranged on the same or on opposite side wall sections of the cartridge holder. Moreover, first and second fixing means may comprise positive locking members arranged at the circumference of the cartridge holder.

In a further preferred embodiment first and/or second fixing means comprise a through opening in a side wall section of the cartridge holder, wherein the through openings are adapted to receive corresponding detent elements of the drive mechanism and/or of the proximal housing component.

Alternatively, it is conceivable that the first and/or second fixing means of the cartridge holder comprise detent elements to be operably engaged with through openings or comparable indentations arranged at an inner or outer circumferential section of the cartridge holder and/or proximal housing component. Additionally or alternatively it is further conceivable, that the first fixing means of the cartridge holder and the second fixing means comprise positive locking members of different type. For instance, the first fixing means may comprise a through opening whereas its second fixing means comprises a radially inwardly or outwardly directed detent element adapted to engage with a corresponding through opening or indentation provided in the proximal housing component.

In a further independent aspect, the invention also refers to a drug delivery device for dispensing of a dose of a medicament that comprises a cartridge holder as described above and a cartridge containing a medicament disposed in the cartridge holder. The cartridge at its distal end comprises a stepped-down neck portion corresponding with an inner socket of the cartridge holder's distal end. The inner socket of the cartridge holder therefore serves as a stop element and as an abutment face for the cartridge to be arranged therein.

The drug delivery device further comprises a drive mechanism directly connected with the cartridge holder and further comprising an axially displaceable piston rod adapted to be operably engaged with a piston of the cartridge. This arrangement or sub-assembly, wherein a drive mechanism is directly interconnected with a cartridge holder, provides an improved force flow during an injection procedure because drive mechanism and cartridge mechanically communicate via a single component of the drug delivery device. Hence, the cartridge holder provides a fixing and retaining means for both, the cartridge and the drive mechanism.

In a further embodiment, the drug delivery device also comprises a proximal housing component directly connected with the cartridge holder. The proximal housing component or body of the drug delivery device serves as a protection means for the drive mechanism and provides an exterior covering.

According to another preferred embodiment, the cartridge holder further comprises a third fixing means corresponding with fixing means of a protective or outer cap to be releasably mounted on the cartridge holder when the drug delivery device is not in use. Protective cap and proximal housing component may form an exterior covering of the drug delivery device and may further provide a particular aesthetic design.

In a further preferred embodiment, the drug delivery device comprises a dose setting means to be operably engaged with a proximal end section of the drive mechanism. By way of the dose setting means, the size of a dose to be dispensed can be adjusted and the process of a dose injection can be triggered. Preferably, dose adjustment is conducted by rotating the dose setting means with respect to the proximal housing component and/or with respect to the drive mechanism. Delivery of the dose and starting of an injection procedure may be triggered by exerting distally directed pressure on the dose setting means, which is typically arranged at a proximal end portion of the drug delivery device.

Preferably, the dose setting means comprises two components, namely a distal portion which is connectable to the drive mechanism and a proximal portion which is connectable to the proximal housing component. Distal and proximal portions of the dose setting means can be separately assembled with respective functional groups of the drug delivery device or respective sub-assemblies during assembly of the drug delivery device.

In a further embodiment, the distal and proximal portion of the dose setting means are adapted to mutually engage upon assembly of proximal housing component and cartridge holder. Here, the distal portion of the dose setting means is pre-assembled and connected to the drive mechanism being interconnected with the cartridge holder. The proximal portion of the dose setting means is preferably pre-assembled with the proximal housing component. Mutual engagement and connection of the two portions of the dose setting means is conducted during final assembly of proximal housing component and cartridge holder or the respective cartridge holder sub-assembly.

In a further independent aspect, the invention also refers to a method of assembly of the drug delivery device, wherein in a first step a cartridge containing a medicament is inserted into a cartridge holder. Thereafter, the cartridge holder is interconnected with a drive mechanism. This way, all thrust-generating and thrust transferring components of a drug delivery device can be interconnected by a single component, namely by the cartridge holder. The cartridge holder therefore serves as a base or as a platform for assembling the drug delivery device. Almost all functional components of the drug delivery device, such like piercing assembly, cartridge, drive mechanism and proximal housing components as well as a protective cap can be directly assembled and interconnected with the cartridge holder. Tolerances of manufacture and assembly can therefore be advantageously reduced.

Additionally, the overall design of the drug delivery device can be universally and individually adapted to varying design requirements by simply exchanging one or several of the components that are to be coupled with the catridge holder. For example, various different proximal housing components or even drive mechanisms can be coupled with the cartridge holder, as long as they comprise an inter-operable interface for establishing a connection with the cartridge holder. This way, a set of inter-operable functional components for a drug delivery device can be provided allowing to exchange particular components, such like cap, body, drive mechanism if required.

In a further preferred embodiment, after interconnecting cartridge holder and drive mechanism, a proximal housing component is interconnected with the cartridge holder, by inserting a proximally protruding portion of the drive mechanism into the proximal housing component.

According to another preferred embodiment, a distal portion of a dose setting means is connected to the drive mechanism prior to an assembly of the proximal housing component and the cartridge holder. Correspondingly, a proximal portion of the dose setting means is pre-assembled with the proximal housing component prior to assembly of said housing component with the cartridge holder. Proximal and distal portions of the dose setting means mutually engage upon assembly of proximal housing component and cartridge holder. The proximal component of the dose setting means is preferably designed as dose button that can be operated by a user, e.g. for setting as well as for dispensing of a dose. The distal and proximal portions of the dose setting means may comprise mutually corresponding fastening means, such like snap-in features that form a positive locking of the two dose setting portions upon assembly of proximal housing component and cartridge holder.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE FIGURES

In the following, preferred embodiments of the invention will be explained in greater detail by making reference to the drawings in which:

FIG. 4 shows the cartridge holder according to FIG. 3 in a vertical longitudinal cross section and FIG. 5 shows the cartridge holder according to FIG. 3 in a horizontal longitudinal cross section, FIG. 6 perspectively illustrates a proximal housing component, FIG. 7 illustrates the housing component according to FIG. 6 in longitudinal cross section, FIG. 8 perspectively illustrates the two-component dose setting means.

DETAILED DESCRIPTION

Figure 1:
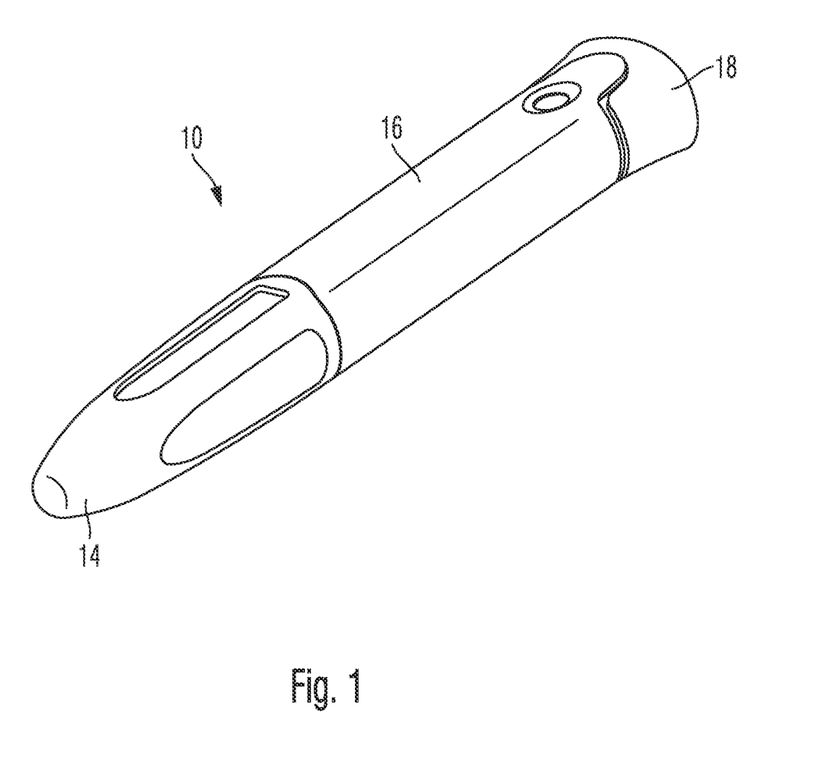
FIG. 1 shows a perspective illustration of the drug delivery device.
Figure 2:
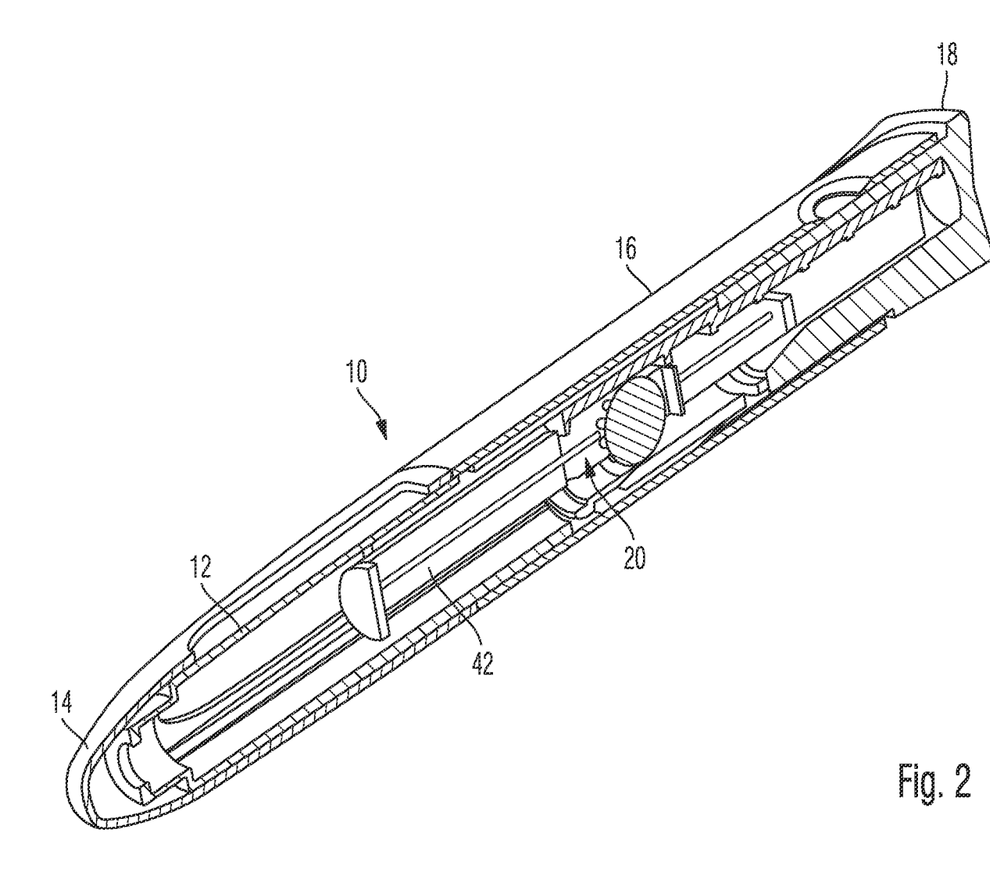
FIG. 2 illustrates the drug delivery device according to FIG. 1 in a cross-sectional perspective view, FIG. 3 separately illustrates the cartridge holder in a perspective view.
Figure 3:
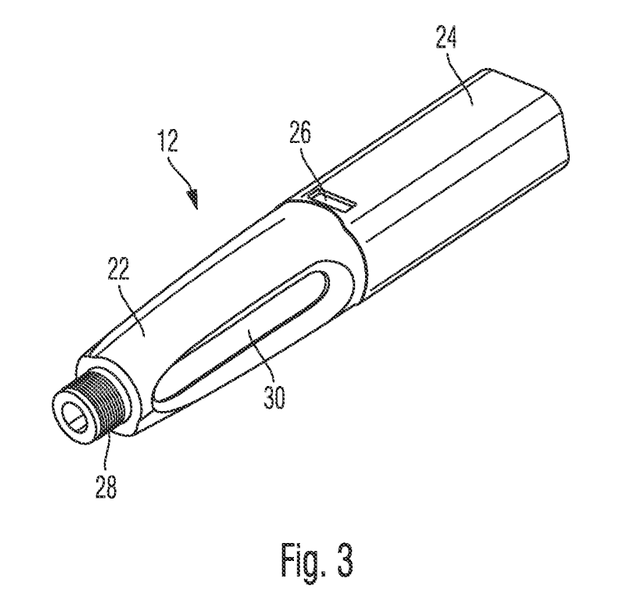
Figure 10:
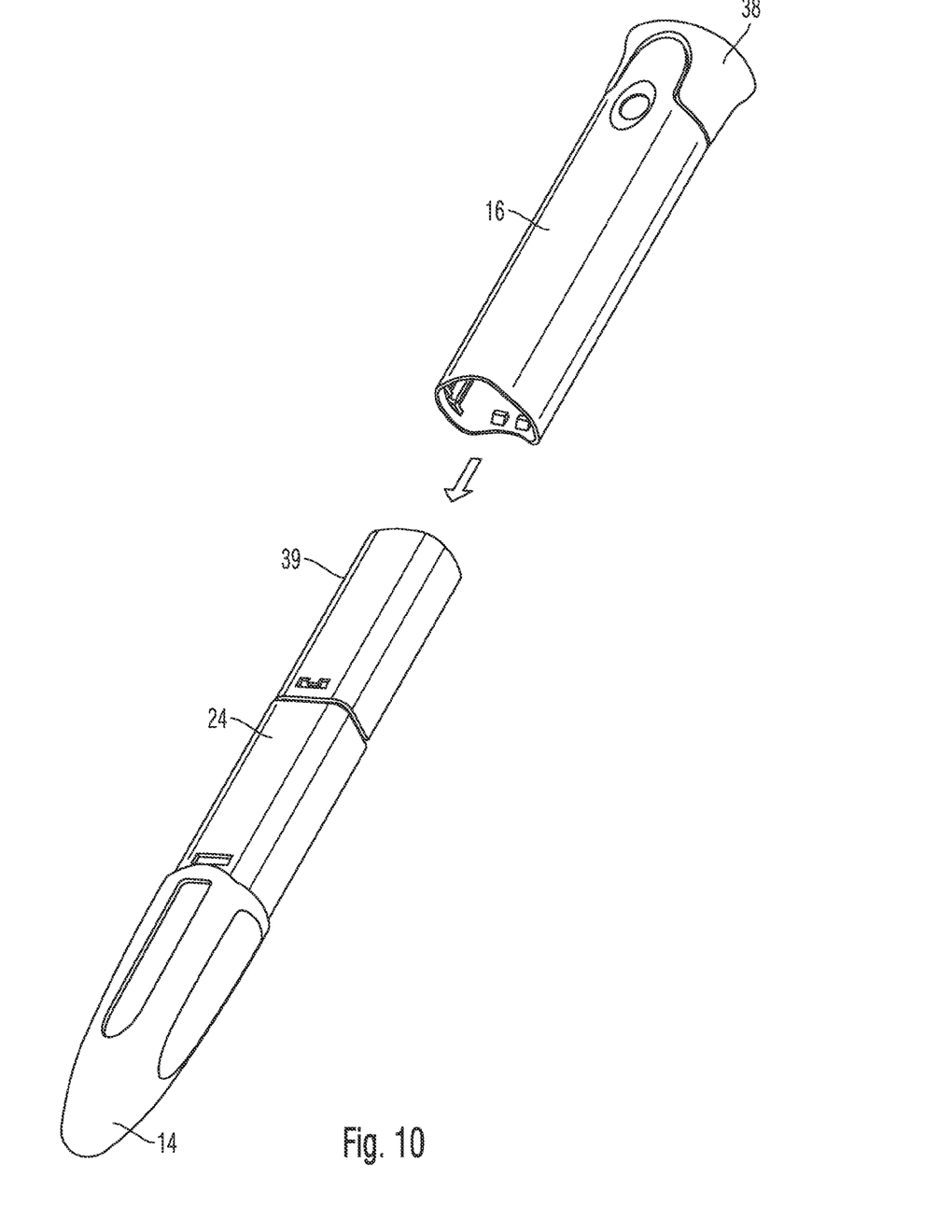

The drug delivery device 10 as illustrated in FIGS. 1, 2 and 10 comprises a cartridge holder 12 that serves as a platform for mounting a plurality of functional components of the drug delivery device thereto. The cartridge holder 12, shown in detail in FIGS. 3 to 5, comprises a distal portion 22 having an inspection window 30, wherein the distal portion 22 is adapted to receive and to retain a cartridge filled with a medicament. The cartridge itself is not explicitly illustrated here.

Figure 4:
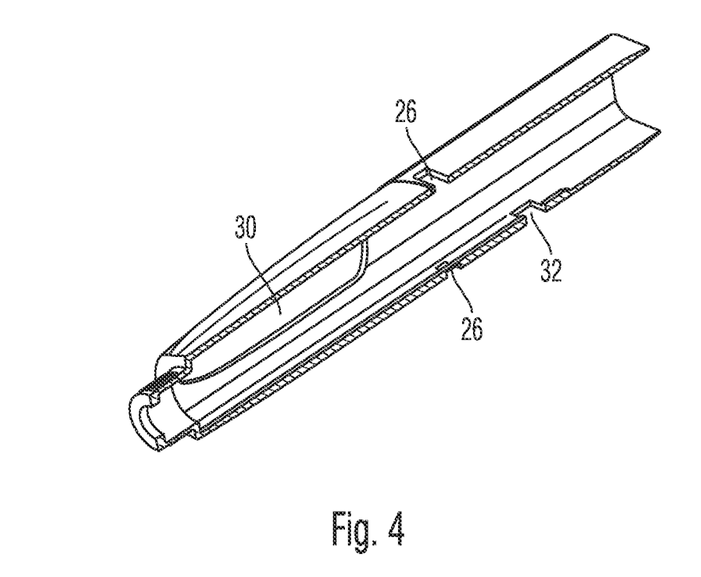

The cartridge holder 12 further comprises a proximal portion 24 that serves to receive at least parts of a drive mechanism 20 having a piston rod 42 to become operably engaged with a piston of the cartridge. The drive mechanism as functional group of the drug delivery device can be connected to the cartridge holder 12 by way of a first fixing means 32, which in the embodiment according to FIG. 4 is designed as a through opening in a side wall section of the proximal portion 24 of the cartridge holder.

Additionally, the cartridge holder 12 comprises a second fixing means 26 being also designed as through opening in a side wall section of the proximal portion 24 of the cartridge holder 12. The second fixing means 26 is adapted to correspond with radially inwardly protruding detent elements 36 of a proximal housing component 16 of the drug delivery device, which is separately illustrated in FIGS. 6 and 7.

The snap-in features 26, 36 provide mutual connection of cartridge holder 12 and proximal housing component 16 of the drug delivery device simply by pushing the proximal housing component or body 16 onto a cartridge holder sub-assembly as illustrated in FIG. 10. Mutual fastening or fixing of cartridge holder 12 and drive mechanism 20 can be realized in a similar manner.

The cartridge holder 12 at its distal end section comprises a threaded stepped-down neck portion 28 which is adapted to receive a piercing assembly that comprises an injection needle to be pierced through a septum of the cartridge and to provide a fluid communication to the inner volume of the cartridge.

Moreover, the cartridge holder 12 comprises a third fixing means, not particularly illustrated here, which is adapted to interact with a corresponding fixing means of the protective cap 14 of the drug delivery device. Cap 14 and body 16 form an exterior covering of the drug delivery device as becomes apparent from FIGS. 1 and 2.

Figures 5, 6, 7:
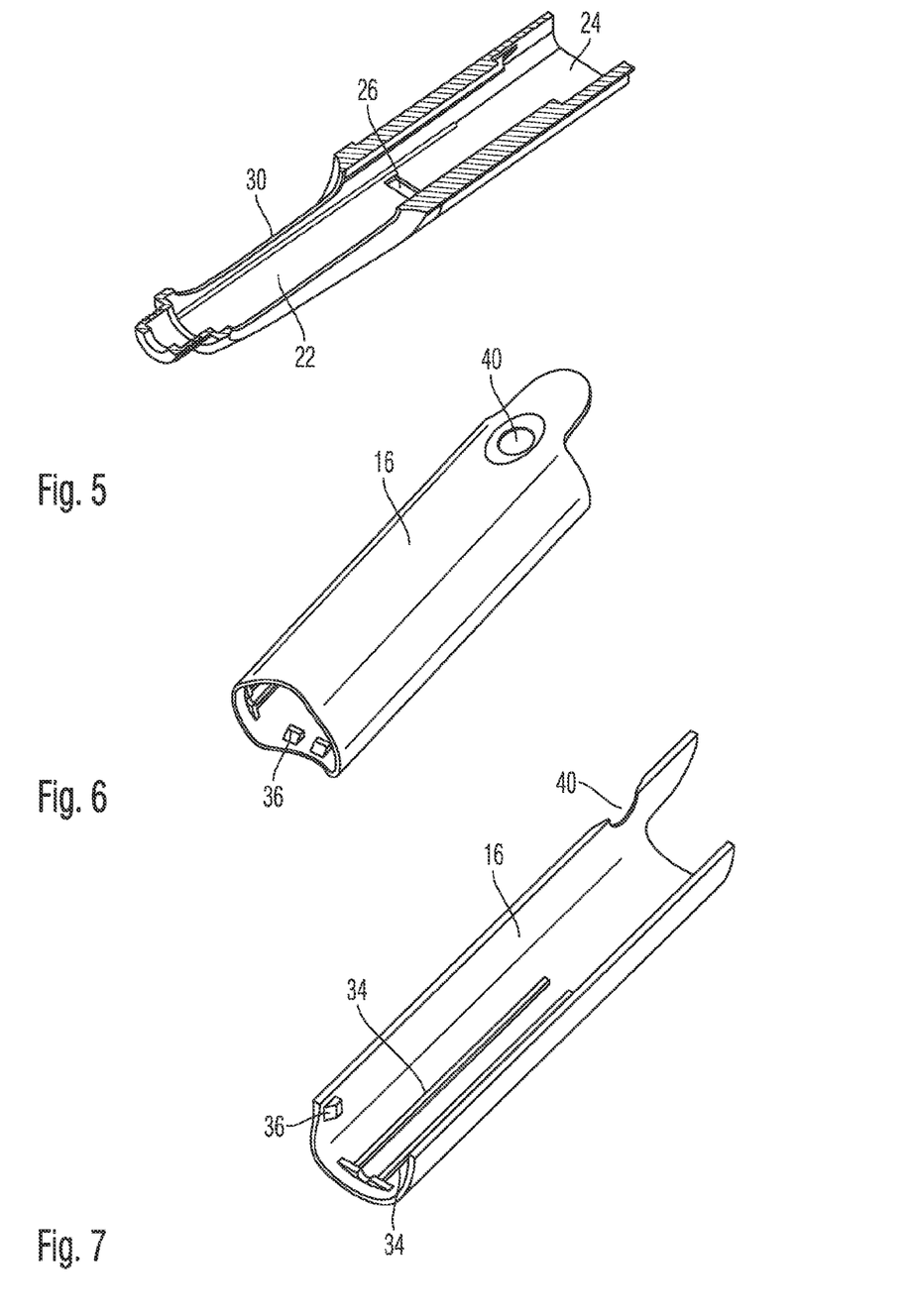
Figure 8:
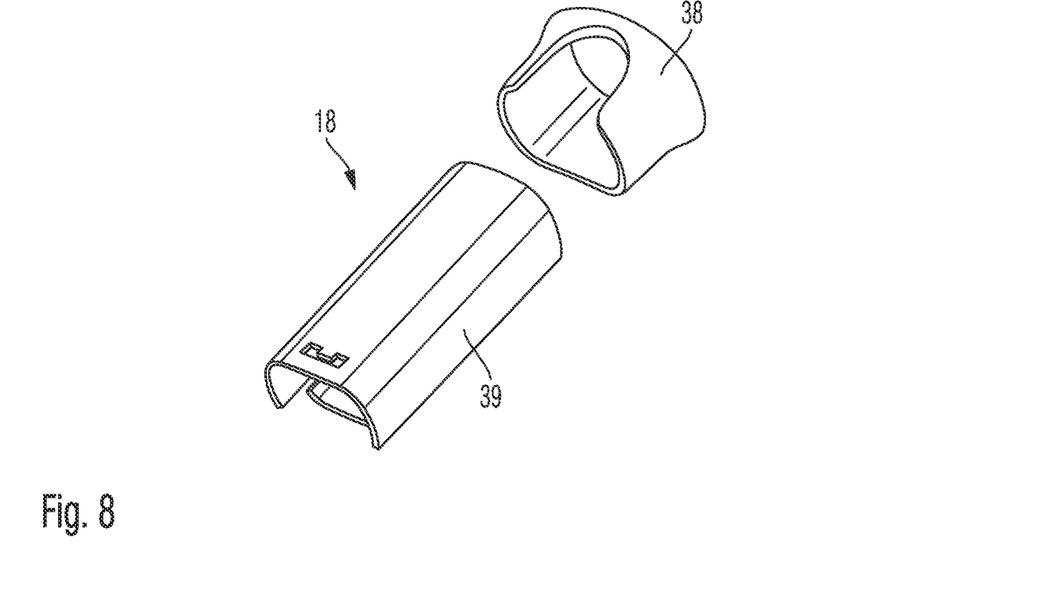

The proximal housing component or body 16 of the drug delivery device is separately illustrated in FIGS. 6 and 7. The body 16 is of substantially cylindrical shape and comprises two substantially parallel extending guiding ribs 34 at an inner side wall. By way of the guiding ribs 34, a dose setting means 18 can be slidably guided therein. The dose setting means 18 is separately illustrated in FIG. 8 and comprises a proximal component 38 and a distal component 39. Preferably, the distal component 39 is slidably disposed in the body 16 by way of the guiding ribs 34 whereas the proximal portion 38 may protrude from the proximal end section of the body 16 as illustrated in FIG. 10. As further indicated in FIG. 7, the body comprises an inspection or indicating window 40, which, in a rather simple embodiment may even be designed as a through opening in a side wall section of the body 16.

Proximal and distal portion 38, 39 of the dose setting means 18 are preferably separately attached to two different sub-assemblies of the drug delivery device in the course of its assembly. Preferably, the distal component 39 is connected to the drive mechanism whereas the proximal component 38 is pre-assembled to the body 16 as illustrated in FIG. 10. Upon final assembly of the drug delivery device, wherein the body 16 is interconnected with the cartridge holder 12 also proximal and distal components 38, 39 of the dose setting or dose injecting means 18 operably engage.

Figure 9:
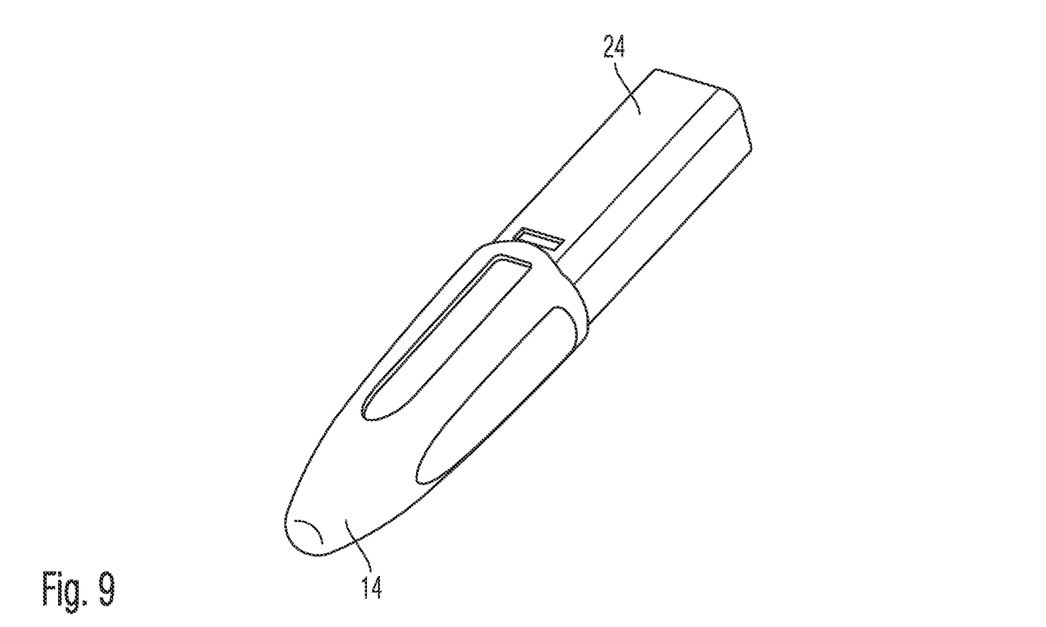
FIG. 9 shows a cartridge holder sub-assembly in a first assembling configuration and FIG. 10 illustrates the final assembly of the drug delivery device.

In FIGS. 9 and 10, a typical method of assembly of the drug delivery device is exemplarily illustrated. In a first step, the cartridge is inserted into the cartridge holder 12 and the protective cap 14 may be optionally attached to the cartridge holder 12 thus forming a cartridge-holder sub-assembly. In a subsequent step of assembly, the drive mechanism 20 is connected to the cartridge holder 12 by at least inserting a distal section of the drive mechanism 20 into the proximal portion 24 of the cartridge holder 12. The drive mechanism 20 may already be interconnected with the distal portion 39 of the dose setting means 18. Alternatively, said dose sleeve 39 may be separately attached to the drive mechanism 20 after the drive mechanism 20 has been connected to the cartridge holder 12.

The dose button 38 is typically pre-assembled with the body 16 and in a final assembly step, the cartridge holder sub-assembly and the body sub-assembly are interconnected by pushing the body sub-assembly onto the cartridge holder sub-assembly in distal direction as indicated in FIG. 10. Upon this final step of assembly, dose button 38 and dose sleeve 39 mutually engage.

The invention claimed is:

1. A cartridge holder for a drug delivery device comprising:
   a distal portion and a proximal portion integrally formed as a single piece, where the distal portion is configured for receiving a cartridge filled with a medicament to be dispensed by the drug delivery device, wherein the distal portion comprises a mount for a piercing assembly, and
   the proximal portion is configured to interconnect to at least part of a drive mechanism having a piston rod to become operably engaged with a piston of the cartridge for expelling a dose of the medicament from the cartridge,
   wherein the proximal portion of the cartridge holder comprises a first lock configured to engage a corresponding lock on the drive mechanism for directly interconnecting the proximal portion of the cartridge holder and drive mechanism,
   wherein the cartridge holder comprises a second lock for interconnecting the proximal portion of the cartridge holder with a proximal housing component configured to house a proximal portion of the drive mechanism, where the first lock and the second lock comprise either a through opening or an indentation.

2. The cartridge holder according to claim 1, wherein the proximal portion comprises a receptacle to receive at least a distal portion of the drive mechanism.

3. The cartridge holder according to claim 1, wherein either the first lock or the second lock comprises a through opening in a side wall section adapted to receive corresponding detent elements of either the drive mechanism or of the proximal housing component.

4. A drug delivery device for dispensing a dose of a medicament comprising:
   a cartridge holder according to claim 1,
   a cartridge containing a medicament and being mounted in the cartridge holder a drive mechanism directly connected with the cartridge holder and having an axially displaceable piston rod adapted to be operably engaged with a piston of the cartridge.

5. The drug delivery device according to claim 4, further comprising a proximal housing component directly connected with the cartridge holder.

6. The drug delivery device according to claim 4, further comprising a dose setting mechanism to be operably engaged with a proximal end section of the drive mechanism for setting and/or dispensing a dose of the medicament.

7. The drug delivery device according to claim 6, wherein the dose setting mechanism comprises a distal portion connectable to the drive mechanism and a proximal portion connectable to the proximal housing component.

8. The drug delivery device according to claim 7, wherein the distal and proximal portions of the dose setting mechanism are adapted to mutually engage each other upon assembly of proximal housing component and cartridge holder.

* * * * *